US012714691B2

(12) United States Patent
Reinhold et al.

(10) Patent No.: US 12,714,691 B2
(45) Date of Patent: Aug. 25, 2026

(54) METHOD OF TREATING TRIPLE-NEGATIVE BREAST CANCER

(71) Applicants: THE UNITED STATES OF AMERICA, AS REPRESENTED BY THE SECRETARY, DEPARTMENT OF HEALTH AND HUMAN SERVICES, Bethesda, MD (US); GENOME RESEARCH LIMITED, London (GB); DANA FARBER CANCER INSTITUTE, Boston, MA (US)

(72) Inventors: William Curtis Reinhold, Rockville, MD (US); Mathew Garnett, Cambridge (GB); Vinodh Nalin Rajapakse, Rockville, MD (US); Yves Pommier, Bethesda, MD (US); Augustin Luna, Brookline, MA (US)

(73) Assignees: The United States of America, as represented by the Secretary, Department of Health and Human Services, Bethesda, MD (US); Genome Research Limited, London (GB); Dana Farber Cancer Institute, Boston, MA (US)

( * ) Notice: Subject to any disclaimer, the term of this patent is extended or adjusted under 35 U.S.C. 154(b) by 125 days.

(21) Appl. No.: 16/967,472

(22) PCT Filed: Feb. 8, 2019

(86) PCT No.: PCT/US2019/017239
§ 371 (c)(1),
(2) Date: Aug. 5, 2020

(87) PCT Pub. No.: WO2019/157300
PCT Pub. Date: Aug. 15, 2019

(65) Prior Publication Data

US 2021/0220329 A1 Jul. 22, 2021

Related U.S. Application Data

(60) Provisional application No. 62/627,926, filed on Feb. 8, 2018.

(51) Int. Cl.
*A61K 31/404* (2006.01)
*A61K 31/131* (2006.01)
(Continued)

(52) U.S. Cl.
CPC .......... *A61K 31/404* (2013.01); *A61K 31/131* (2013.01); *A61K 31/282* (2013.01);
(Continued)

(58) Field of Classification Search
CPC .. A61K 31/282; A61K 45/06; A61K 31/4402; A61K 31/337; A61K 31/475;
(Continued)

(56) References Cited

U.S. PATENT DOCUMENTS

2014/0186872 A1* 7/2014 Feve ....................... A61P 35/00
546/342

FOREIGN PATENT DOCUMENTS

| | | | |
|---|---|---|---|
| GB | 2162061 * | 1/1986 | ............. A61K 9/229 |
| WO | WO-2005097107 A2 * | 10/2005 | ........... A61K 31/404 |
| WO | WO-2016115171 A1 * | 7/2016 | |

OTHER PUBLICATIONS

Morrison et al., "Oxyphenisatin acetate (NSC 59687) triggers a cell starvation response leading to autophagy, mitochondrial dysfunction, and autocrine TNFalpha-mediated apoptosis" in Cancer Medicine, 2013, pp. 687-700. (Year: 2013).*

(Continued)

*Primary Examiner* — Blessing M Fubara
(74) *Attorney, Agent, or Firm* — McDonnell Boehnen Hulbert & Berghoff LLP

(57) ABSTRACT

The disclosure provides a method of treating triple negative breast cancer in a patient, comprising administering a therapeutically effective amount of a compound selected from oxyphenisatin, oxyphenisatin acetate, and bisacodyl, or the pharmaceutically acceptable salts or hydrates of any of the foregoing to the patient. The disclosure also provides methods of using oxyphenisatin or bisacodyl, or a salt or hydrate thereof, as a first active agent in combination with one or more additional active agents to treat triple negative breast (Continued)

cancer. The disclosure further provides methods for determining whether a patient suffering from triple negative breast cancer would be responsive to treatment with oxyphenisatin or bisacodyl.

20 Claims, 13 Drawing Sheets

(51) Int. Cl.

| | |
|---|---|
| ***A61K 31/282*** | (2006.01) |
| ***A61K 31/337*** | (2006.01) |
| ***A61K 31/4402*** | (2006.01) |
| ***A61K 31/475*** | (2006.01) |
| ***A61K 31/513*** | (2006.01) |
| ***A61K 31/52*** | (2006.01) |
| ***A61K 31/675*** | (2006.01) |
| ***A61K 31/704*** | (2006.01) |
| ***A61K 31/7068*** | (2006.01) |
| ***A61K 33/243*** | (2019.01) |
| ***A61N 5/10*** | (2006.01) |
| ***A61P 35/00*** | (2006.01) |

(52) U.S. Cl.

CPC ........ *A61K 31/337* (2013.01); *A61K 31/4402* (2013.01); *A61K 31/475* (2013.01); *A61K 31/513* (2013.01); *A61K 31/52* (2013.01); *A61K 31/675* (2013.01); *A61K 31/704* (2013.01); *A61K 31/7068* (2013.01); *A61K 33/243* (2019.01); *A61N 5/10* (2013.01); *A61P 35/00* (2018.01)

(58) Field of Classification Search

CPC .. A61K 31/704; A61K 31/513; A61K 31/131; A61K 31/7068; A61K 31/52; A61K 31/404; A61K 33/243; A61K 31/675; A61P 35/00; A61N 5/10

See application file for complete search history.

(56) References Cited

OTHER PUBLICATIONS

Wang et al., "Locoregional and distant recurrences after breast conserving therapy in patients with triple-negative breast cancer: A meta-analysis," in Surgical Oncology, 11 (2013) 247-255. (Year: 2013).*

Ford-Brown in the 1999 Dissertation. (Year: 1999).*

Rajapakse et al., "Integrative analysis of pharmacoggenomics in major cancer cell line databases using CellMinerCDB" in bioRxiv preprint doi: https://doi.org/10.1101/292904, Apr. 2, 2018. (Year: 2018).*

7. https://en.wikipedia.org/wiki/Oxyphenisatine (first archived Aug. 9, 2012) (Year: 2012).*

Kabraji et al., "AKT1low quiescent cancer cells persist after neoadjuvant chemotherapy in triple negative breast cancer" in Breast Cancer Research, 19:88 (2017). (Year: 2017).*

Bethanie L. Morrison et al., "Oxyphenisatin acetate (NSC 59687) triggers a cell starvation response leading to autophagy, mitochondrial dysfuntion, and autocrine TNF alpha-mediated apoptosis", Cancer Medicine, vol. 2, No. 5, Oct. 1, 2013, 14 pages.

Christina Trojel-Hansen et al., "Novel small molecule drugs inhibit tumor cell metabolism and show potent anti-tumorigenic potential", Cancer Chemother Pharmocol, vol. 68, 2011, 12 pages.

International Search Report issued in International Application No. PCT/US2019/017239 filed Feb. 8, 2019, report Issued Apr. 5, 2019, 5 pages.

Jihu Dong et al., "Bisacodyl and its cytotoxic activity on human glioblastoma stem-like cells. Implication of inosital 1,4,5-triphosphate receptor dependent calcium signaling", Biochimica et Biophysica Acta, vol. 1864, 2017, 10 pages.

Maria Zeniou et al., "Chemical Library Screening and Structure-Function Relationship Studies Identify Bisacodyl as a Potent and Selective Cytotoxic Agent Towards Quiescent Human Glioblastoma Tumor Stem-Like Cells", PLOS One, Aug. 13, 2015, 35 pages.

Muhammed K. Uddin et al., "Syntheses and antiproliferative evaluation of oxyphenisatin derivatives", Bioorganic & Medicinal Chemistry Letters, vol. 17, No. 10, Apr. 27, 2007, 4 pages.

Tarah Ballinger et al., "Triple Negative Breast Cancer-Review of Current and Emerging Therapeutic Strategies", Oncology & Hematology Review, vol. 12, No. 2, Jan. 1, 2016, 6 pages.

Written Opinion issued in International Application No. PCT/US2019/017239 filed Feb. 8, 2019, report issued Apr. 5, 2019, 9 pages.

International Preliminary Report on Patentability issued in Application No. PCT/US2019/017239 on Aug. 11, 2020, 7 pages.

* cited by examiner

| Cell Lines | # Lines | # Lines (Median) | # Drugs | DNA Variant | mRNA Exp | DNA Copy | DNA (Meth.) | Mir Exp. | Protein Exp. | # Molecular |
|---|---|---|---|---|---|---|---|---|---|---|
| NCI-60 | 60 | 57 | 21,768 | 9,307 | 25,040 | 23,232 | 17,553 | 360 | 162 (RPPA) | 75,711 |
| GDSC | 1080 | 900 | 297 | 16,532 | 19,562 | - | 17,580 | NA | NA | 53,674 |
| CCLE | 1036 | 491 | 24 | 1,667 | 19,851 | 23,316 | - | - | -(RPPA) | 44,834 |
| CTRP | 823 | 751 | 481 | 1,667 | 19,851 | 23,316 | - | - | -(RPPA) | 44,834 |
| NCI-SCLC | 67 | 66 | 526 | NA | 17,804 | NA | NA | NA | NA | 17,804 |

Fig. 2A

| Cell Lines | NCI-60 | GDSC | CCLE | CTRP | | DRUGS | NCI-60 | GDSC | CCLE | CTRP |
|---|---|---|---|---|---|---|---|---|---|---|
| NCI-60 | 60 | 55 | 44 | 41 | | NCI-60 | 21,768 | 109 | 21 | 63 |
| GDSC | | 1080 | 671 | 597 | | GDSC | | 297 | 15 | 74 |
| CCLE | | | 1036 | 823 | | CCLE | | | 24 | 16 |
| CTRP | | | | 823 | | CTRP | | | | 481 |

Fig. 2B

| Cell Lines | NCI-SCLC | GDSC | CCLE | CTRP | | DRUGS | NCI-SCLC | GDSC | CCLE | CTRP |
|---|---|---|---|---|---|---|---|---|---|---|
| NCI-SCLC | 67 | 40 | 36 | 27 | | NCI-SCLC | 526 | 109 | 21 | 119 |
| GDSC | | 59 | 39 | 29 | | GDSC | | 297 | 15 | 71 |
| CCLE | | | 53 | 39 | | CCLE | | | 24 | 14 |
| CTRP | | | | 39 | | CTRP | | | | 481 |

Fig. 2C

METHOD OF TREATING TRIPLE-NEGATIVE BREAST CANCER

CROSS REFERENCE TO RELATED APPLICATION

This application is a § 371 US National Stage application of International Application No. PCT/US2019/017239 filed 8 Feb. 2019, and claims priority to U.S. Provisional Patent Application No. 62/627,926 filed 8 Feb. 2018. Each of these applications are incorporated herein by reference in their entireties.

BACKGROUND

Breast cancer remains one of the most common and deadly cancers. It is the most commonly diagnosed cancer in women, with approximately 1.7 million cases each year. It is the number one cause of death from cancer in women.

Breast cancer is diagnosed based on the presence (or absence) of three types of receptors, estrogen receptors (ER), progesterone receptors (PGR), and human epidermal growth factor receptor 2 (HER2 or ERBB2). Cancers that exhibit at least one of the receptor types can be treated with drugs, such as hormone therapies for ER and PGR tumors or anti-HER2 therapies, which specifically target these receptors. Triple negative breast cancer (TNBC) tumors exhibit none of these receptors.

Approximately 15-20% of breast cancers are triple negative. These cancers can be treated with cytotoxic chemotherapy, surgery, or radiation. However, TNBC tends to more aggressive and more likely to reoccur than breast cancers with hormone or HER2 receptors. Commonly used chemotherapy drugs for the treatment of TNBC includes use of anthracycline class drugs, especially doxorubicin and epirubicin, taxane class drugs, antimetabolites, alkylating agents, and *vinca* alkaloids. Drug resistant cancers are known to develop following treatment with cytotoxic chemotherapeutic agents, limiting the time any such agent will be effective. Relapse rates following chemotherapy are approximately 80% in TNBC patients. TNBC is more prevalent in pre-menopausal women than in older women. Median survival times are poorer for patients with TNBC. For this reason additional therapies for the treatment of triple negative breast cancer are needed. This disclosure fulfils this need and provides additional advantages.

SUMMARY

The disclosure provides a method of treating triple negative breast cancer in a patient, comprising administering a therapeutically effective amount of a compound selected from oxyphenisatin, oxyphenisatin acetate (Acetalax), oxyphenisatin, bisacodyl, and the pharmaceutically acceptable salts and hydrates of any of the foregoing to the patient.

The disclosure discusses the inventor's development of CellMiner and CellMinerCDB, unique web-based tools that facilitate interactive exploration of major cancer cell line pharmacogenomic data sources. Development of these tools was central to the discovery that oxyphenisatin and bisacodyl could be used to treat cancer, including breast, colon, and ovarian cancer, and that these drugs were particularly useful for treating triple negative breast cancer.

Oxyphenisatin acetate (Acetalax) and bisacodyl have been discovered to be surprisingly efficacious for treating triple negative breast cancer, a disease that currently has no highly effective treatment. Oxyphenisatin acetate and bisacodyl have been found, surprisingly, to be more effective against most triple negative breast cancer cell lines than against breast cancer cell lines generally, a very unusual activity pattern.

The disclosure includes the use of a compound selected from oxyphenisatin, oxyphenisatin acetate, and bisacodyl, and the pharmaceutically acceptable salts and hydrates of any of the foregoing for treating triple negative breast cancer.

The disclosure also provides a pharmaceutical composition for use in treating triple negative breast cancer comprising a therapeutically effective amount of a compound selected from oxyphenisatin acetate, oxyphenisatin, bisacodyl, and the pharmaceutically acceptable salts and hydrates of any of the foregoing.

The disclosure provides a method for identifying those cancer patients who are likely to benefit from treatment with oxyphenisatin, oxyphenisatin acetate, or bisacodyl and treating their cancer by administration of oxyphenisatin, oxyphenisatin acetate, or bisacodyl. The disclosure includes a method of treating a patient having a triple negative breast cancer, the method comprising determining whether the patient has a tumor that has elevated expression of IGF1, SCL31A1, ABCA12, SPIB, or PIK3R1; and if the patient has a tumor that has elevated expression of IGF1, SCL31A1, ABCA12, SPIB, or PIK3R1; administering a compound selected from oxyphenisatin acetate, oxyphenisatin, bisacodyl, and the pharmaceutically acceptable salts and hydrates of any of the foregoing to the patient.

BRIEF DESCRIPTION OF THE DRAWINGS

FIG. 2. Data source comparisons. A. Summary of molecular and drug activity data for 5 data sources included in CellMinerCDB. For molecular data types, the numbers indicate the number of genes with a particular data type. GDSC gene-level mutation and methylation data were prepared from raw data as part of the development of CellMinerCDB. Asterisks indicate molecular data under development, but not publicly available. B. and C. Cell line and drug overlaps between data sources.

FIG. 6. Activity plots as a function of NCI-60 cell line. In FIG. 6A group 1 cell lines are breast cancer cell lines, Group 3 are colon cancer cell lines, and Group 7 are ovarian cancer cell lines. A full listing of the cell lines is provided in example 5.

FIG. 9. Plot of observed vs. predicted Acetalax activity in GDSC breast cancer cell lines.

DETAILED DESCRIPTION

Terminology

Figure 1:
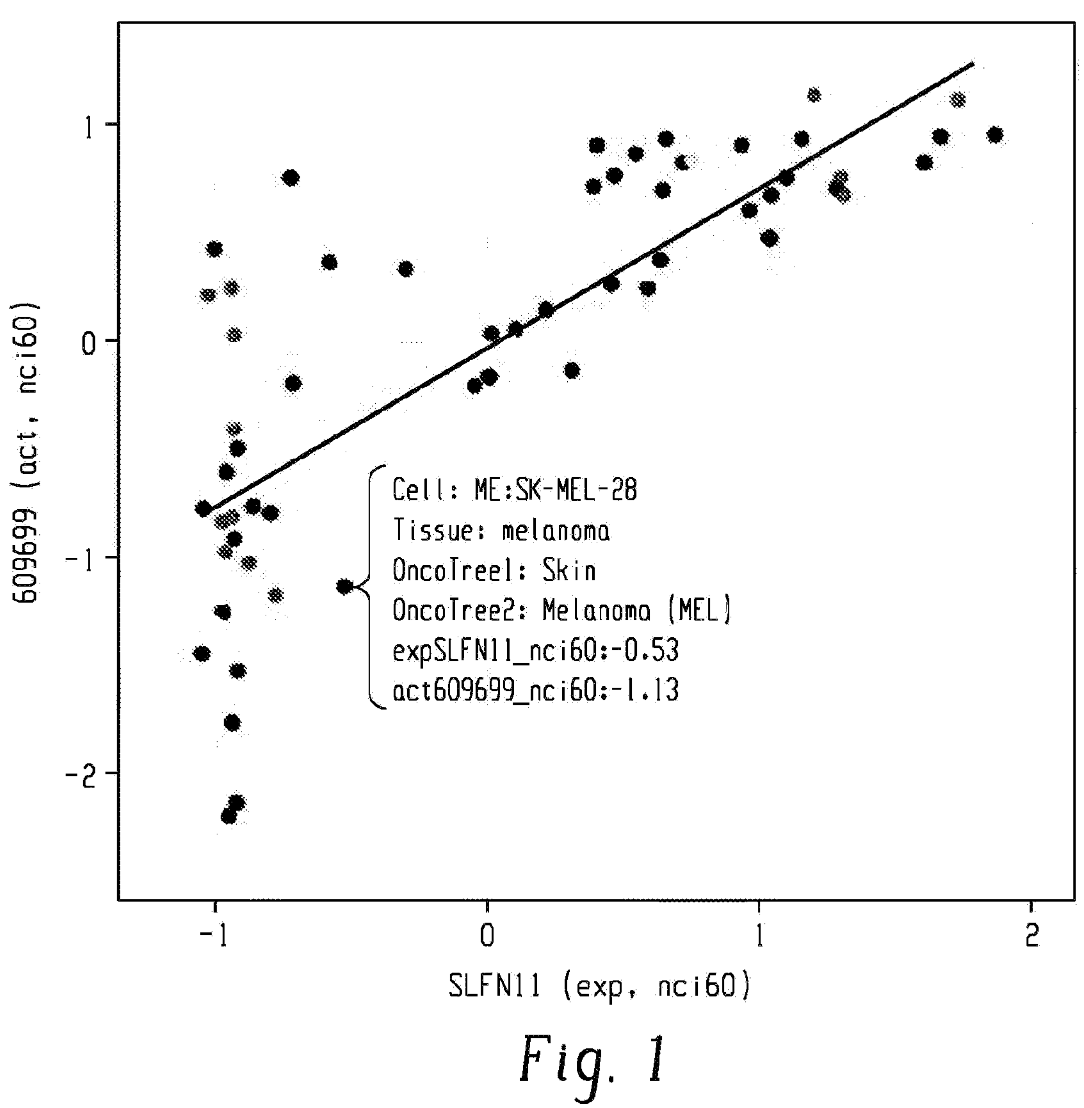
FIG. 1. Plot of topotecan (609699) activity (Y-axis) vs. expression of SFLN11 (X-axis), a helicase that sensitizes cancer cells to DNA-damaging agents in the NCI-60 tumor cell lines.

Before describing the invention in detail, it will be helpful to have these definitions of terms used in the claims and elsewhere in the specification. Compounds are described using standard nomenclature.

Unless otherwise indicated, the disclosure is not limited to specific procedures, starting materials, or the like, as such may vary. It is also to be understood that the terminology used herein is for the purpose of describing particular embodiments only and is not intended to be limiting. Unless clearly contraindicated by the context each compound name includes the free acid or free base form of the compound as well as hydrates and pharmaceutically acceptable salts of the compound.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The open ended term "comprising" encompasses the terms "consisting of" and "consisting essentially of."

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

The phrases "for example," "for instance," "such as," or "including" are meant to introduce examples that further clarify more general subject matter. These examples are provided only as an aid for understanding the disclosure, and are not meant to be limiting in any fashion.

The "first active compound" as used herein mean a compound selected from any of oxyphenisatin, oxyphenisatin acetate, and bisacodyl, and pharmaceutically acceptable salts and hydrates of any of the foregoing. The terms "oxyphenisatin" and "bisacodyl" include all pharmaceutically acceptable forms of those compounds, such as pharmaceutically acceptable salts or hydrates, unless the context clearly indicates otherwise.

"Pharmaceutical compositions" are compositions comprising at least one active agent, such as oxyphenisatin acetate (Acetalax) or bisacodyl, and at least one other substance, such as a carrier, excipient, or diluent. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

The term "carrier" applied to pharmaceutical compositions of the invention refers to a diluent, excipient, or vehicle with which an active compound is provided.

A "therapeutically effective amount" as used herein means an amount effective, when administered to a patient, to provide a therapeutic benefit such as an amelioration of at least a symptom of the disorder, decrease the frequency or severity of symptoms, or effect a change in a clinical marker for a disease or disorder, slowing the progression of a disease or disorder, halting the progression of a disease or disorder, or reversing the course of a disorder. In the context of triple negative breast cancer, a "therapeutically effective amount" also includes an amount sufficient for any of slowing the rate of tumor growth and formation, slowing the metastasis of the cancer, halting tumor growth, halting the formation of new tumors, halting the metastasis of the cancer, reducing tumor size, reducing the number of tumors, causing a remission so cancer is no longer observable in the patient, or reducing any marker of triple negative breast cancer in the patient.

Acetalax and Bisacodyl

Oxyphenisatin acetate (tradenames ACETALAX, CONTAX, ACETOPHENOLISATIN, BROCATINE, DIPHESATIN, CAS Reg. No. 115-33-3) is a small molecule drug long marketed for the treatment of constipation. It is thought that the oxyphenisatin pharmacophore is a metabolic modulator. Acetalax has the following structure:

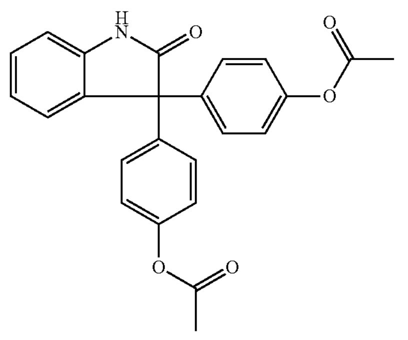 [SMILES: CC(=O)Oc1ccc(C2(c3ccc(OC(C)=O)cc3)C(=O)Nc3ccccc32)cc1]

Oxyphenisatin acetate is a prodrug of oxyphenisatin (CAS reg. no. 125-13-3), which is also active as a laxative.

Bisacodyl (tradenames FLEET, PURGA, DULCOLAX, CORRECTOL, and others, CAS Reg. No. 603-50-9) is a stimulant laxative used to treat constipation or to clear the colon prior to medical procedures, such as a colonoscopy. Bisacodyl stimulates enteric nerves to cause colonic contractions. It is also a contact laxative; increasing fluid and salt secretion. Bisacodyl has negligible action on the small intestine as stimulant laxative mainly promote evacuation of the colon. Bisacodyl has the structure:

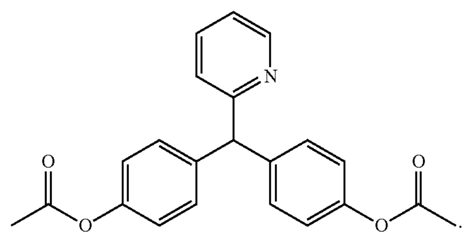 [SMILES: CC(=O)Oc1ccc(C(c2ccc(OC(C)=O)cc2)c2ccccn2)cc1]

Pharmaceutical Preparations

Oxyphenisatin, oxyphenisatin acetate, and bisacodyl, and the pharmaceutically acceptable salts and hydrates of any of the foregoing can be administered as neat chemicals but are preferably administered as a pharmaceutical composition. Accordingly, the disclosure provides pharmaceutical compositions comprising a first active compound selected from any of oxyphenisatin, oxyphenisatin acetate, and bisacodyl, and the pharmaceutically acceptable salts and hydrates oxyphenisatin acetate together with at least one pharmaceutically acceptable carrier. The pharmaceutical composition may contain a compound or salt of oxyphenisatin, oxyphenisatin acetate, or bisacodyl as the only active agent, or may contain one or more additional active agents.

The first active compound may be administered orally, topically, parenterally, by inhalation or spray, sublingually, transdermally, intravenously, intrathecally, via buccal administration, or rectally, or by other means, in dosage unit formulations containing conventional pharmaceutically acceptable carriers. In certain embodiments the first active compound is administered orally. In certain embodiments the first active compound is administered subcutaneously or intravenously. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions can be formulated for oral administration. These compositions contain between 0.1 and 99 weight % (wt. %) of a compound of and usually at least about 5 wt. % of a the first active compound. Some embodiments contain from about 25 wt. % to about 50 wt. % or from about 5 wt. % to about 75 wt. % of the first active compound.

Methods of Use

This disclosure provides a method of treating triple negative breast cancer in a patient, comprising administering a therapeutically effective amount of a compound selected from oxyphenisatin acetate, oxyphenisatin, bisacodyl, and the pharmaceutically acceptable salts or hydrates of any of the foregoing. The disclosure provides additional methods of treating cancer in a patient, including methods of treating ovarian cancer and colon cancer, comprising administering a therapeutically effective amount of a compound selected from oxyphenisatin acetate, oxyphenisatin, bisacodyl, and the pharmaceutically acceptable salts and hydrates of any of the foregoing to the patient. In certain embodiments the patient has a BRACA1 or BRACA2 gene mutation. In certain embodiments the patient has a tumor, such as a triple negative breast cancer tumor, a colon cancer tumor, or an ovarian cancer tumor in which expression of IGF1, SCL31A1, ABCA12, SPIB, or PIK3R1 is elevated.

The disclosure includes a method of treating a patient having a triple negative breast cancer, the method comprising determining whether the patient has a tumor that has elevated expression of a biomarker for response to oxyphenisatin, oxyphenisatin acetate, or bisacodyl treatment. These biomarkers include IGF1, SCL31A1, ABCA12, SPIB, or PIK3R1. IF the patient has a tumor that has elevated expression of a biomarker such as IGF1, SCL31A1, ABCA12, SPIB, or PIK3R1 the patient is administered a compound selected from oxyphenisatin acetate, oxyphenisatin, bisacodyl, and the pharmaceutically acceptable salts and hydrates of any of the foregoing to the patient. Elevated expression of biomarkers can be measured by quantitating transcription expression of the gene for the biomarker or by another method such as directly quantitating the level of biomarker, for example using a marker specific antibody.

The oxyphenisatin or bisacodyl may be administered by any method of pharmaceutical administration, including oral, topical, parenteral, intravenous, subcutaneous injection, intramuscular injection, inhalation or spray, sublingual, transdermal, intravenous, intrathecal, buccal, and rectal administration. In certain embodiments administration of oxyphenisatin, oxyphenisatin acetate, or bisacodyl is oral or parenteral.

Methods of treatment include providing certain dosage amounts of the first active compound to a patient. Dosage levels of oxyphenisatin, oxyphenisatin acetate, or bisacodyl of from about 0.01 mg to about 140 mg per kilogram of body weight per day are useful in the treatment of the above-indicated conditions (about 0.5 mg to about 1 g per patient per day). In certain embodiments 0.1 mg to 5000 mg, 1 mg to 2000 mg, 1 mg to 1000 mg, 1 mg to 500 mg, 1 mg to 200 mg, 1 mg to 100 mg, 1 mg to 50 mg, 10 mg to 5000 mg, 10 mg to 2000 mg, 10 mg to 1000 mg, 10 mg to 500 mg 10 mg to 300 mg, 10 mg to 200 mg, 10 mg to 100 mg, 50 mg to 5000 mg, 50 mg to 2000 mg, 50 mg to 1000 mg, 50 mg to 500 mg, 50 mg to 200 mg, of the oxyphenisatin, oxyphenisatin acetate, or bisacodyl are provided daily to a patient. In certain embodiments 0.1 mg to 5000 mg, 1 mg to 2000 mg, 1 mg to 1000 mg, 1 mg to 500 mg, 1 mg to 200 mg, 1 mg to 100 mg, 1 mg to 50 mg, 10 mg to 5000 mg, 10 mg to 2000 mg, 10 mg to 1000 mg, 10 mg to 500 mg 10 mg to 300 mg, 10 mg to 200 mg, 10 mg to 100 mg, 50 mg to 5000 mg, 50 mg to 2000 mg, 50 mg to 1000 mg, 50 mg to 500 mg, 50 mg to 200 mg per dose of oxyphenisatin, oxyphenisatin acetate, or bisacodyl are provided to the patient.

Frequency of dosage may also vary depending the particular disease treated. However, for treatment of breast cancer, a dosage regimen of 4 times daily or less is preferred, and a dosage regimen of 1 or 2 times daily is particularly preferred. Treatment regimens may also include administering the first active compound (oxyphenisatin, oxyphenisatin acetate, or bisacodyl) to the patient for a number of consecutive days, for example for at least 5, 7, 10, 15, 20, 25, 30, 40, 50, or 60 consecutive days. In certain embodiments the first active compound is administered for a period of 1 to 10 weeks and the amount and frequency of dosage is such that concentration of the compound in the patient's plasma in never less than 50% of the patient's plasma Cmax.

Treatment regimens may also include administering the first active compound to the patient for a number of days prior to cancer surgery (surgery to remove tumors including mastectomy and lumpectomy). For example the first active compound may be administered to the patient for a number of consecutive days at 1 to 4 months prior to surgery. Treatment regimens may also include administering the first active compound to the patient in conjunction with radiation therapy, e.g., before, during or after radiation therapy.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disorder for the patient undergoing therapy.

Combination Therapy

The first active compound, oxyphenisatin, oxyphenisatin acetate, or bisacodyl, may be used alone to treat triple negative breast cancer, ovarian cancer, or colon cancer, or in combination with at least one additional active compound. Combination use includes an administering of the first active compound and additional active compound in a single dosage form, or in separate dosage forms either simultaneously or sequentially.

Suitable doses for the first active compound when used in combination with a second active agent are generally as described above. Doses and methods of administration of other therapeutic agents can be found, for example, in the manufacturer's instructions in the Physician's Desk Reference. In certain embodiments, the combination administration of the first active compound with the additional active compound results in a reduction of the dosage of the additional active compound required to produce a therapeutic effect (i.e., a decrease in the minimum therapeutically effective amount). Thus, preferably, the dosage of an additional active compound in a combination or combination treatment method is less than the maximum dose advised by the manufacturer for administration of the additional active compound without combination administration of a the first active compound. In certain embodiment this dosage is less than ¾, less than ½, less than ¼, or even less than 10% of the maximum dose advised by the manufacturer for the additional active compound when administered without combination administration of the first active compound.

When treating triple negative breast cancer, ovarian cancer or colon cancer, with "a first active compound" as described herein, the additional active compound can be an anthracycline class drug, a taxane class drug, an antimetabolite, an alkylating agent, a platinum agent, or a *vinca* alkaloid. For example the additional active agent can be daunorubicin, doxorubicin, epirubicin, idarubicin, valrubicin, docetaxel, paclitaxel, abraxane, taxotere, 5-fluorouracil, 6-mercaptopurine, capecitabine, cytarabine, gemcitabine, mechlorethamine, cyclophosphamide, chlorambucil, melphalan, ifosfamide, cisplatin, carboplatin, oxaliplatin, nedaplatin, vinblastine, vincristine, vindesine, vinorelbine, vincaminol, vineridine, or vinburnine. In certain embodiments the additional active agent is doxorubicin or epirubicin.

The additional active agent can also include drugs used to treat breast cancer or ovarian cancer. Drugs used to treat breast cancer include adriamycin, capecitabine, carboplatin, cyclophosphamide, cytoxan, docetaxel, doxorubicin, epirubicin, fluorouracil (5FU), gemcitibine, methotrexate, mitomycin, mitoxantrone, paclitaxel, palbociclib, Taxol, and vincristine. Drugs used to treat ovarian cancer include altretamine, bevacizumab, carboplatin, cisplatin, docetaxel, paclitaxel (Taxol), capecitabine, cyclophosphamide, etoposide, gemcitabine, ifosfamide, irinotecan, liposomal doxorubicin, melphalan, pemetrexed, topotecan, and vinorelbine.

CellMinerCDB

The inventors have developed CellMiner (discover.rtci.nih.gov) and CellMinerCDB (discover.rtci.nih.gov), unique web-based tools that facilitate interactive exploration of major cancer cell line pharmacogenomic data sources. Identifying the molecular determinants of drug response can inform cancer treatment decisions. Cancer cell lines offer a primary, tractable starting point for identifying these determinants and understanding their mechanistic role. Pharmacogenomic data sources provide matched molecular and drug activity profiling data for leading cancer cell line panels, including those of the NCI-60 (National Cancer Institute-60), GDSC (Genomics of Drug Sensitivity in Cancer), CCLE (Cancer Cell Line Encyclopedia), and CTRP (Clinical Trials Reporting Program). CellMiner and CellMinerCDB are the only web application that allows easy, interactive exploration of all major cancer cell line pharmacogenomic data sources. CellMiner focuses on the NCI-60, while CellMinerCDB integrates both data and exploratory statistical analyses both within and across data sources. GDSC molecular and drug response data are presented to illustrate the value of CellMinerCDB, in assessing molecular and drug data reproducibility, potential drug response and gene regulatory determinants.

A critical aim of precision medicine is to connect drug responses and their potential molecular genomic determinants to ultimately gain a mechanistic understanding of drug function. Tumor sample data provide information on recurrent "cancer functional events." However, associating tumor sample molecular features with specific drug treatments is especially challenging because of the typically encountered diversity of patient experiences and tumor heterogeneity, and limited amount of information available on each patient. The relative homogeneity and ability to accumulate data of cancer cell lines is advantageous, making them the primary starting point for resolving cell intrinsic drug response mechanisms. The use of CellMiner and CellMinerCDB to expand development of cancer cell line pharmacogenomic data and discover additional compounds useful for treating cancer is exemplified by this disclose.

The CellMiner NCI-60 database provides drug activity data for over 21,000 compounds, together with the widest range of molecular profiling data, including gene expression, mutation, copy number, methylation, and protein expression. The GDSC and CCLE collections focus on drug activity data for clinically relevant drugs over larger cell line sets, together with a growing array of molecular profiling data. The CTRP database provides independent drug activity data for nearly 500 compounds over cell lines spanning most of the CCLE collection and much of the GDSC collection. The source-specific portals for each allow deep exploration of their associated data sets, but they leave untapped an opportunity for cross-database analyses. Substantial overlaps in both cell lines and tested drugs allow integrative analyses building on the complementary strengths of the cancer cell line data sets. But data complexity and mundane sources of friction, such as differently named entities (cell lines, drugs), make working across databases challenging, even for those with informatics training.

Use of CellMinerCDB drug activity as a function of gene expression is demonstrated by FIG. 1. In the example shown in FIG. 1 the drug is topotecan (NSC 609699) and the gene expression level is SLFN11. The CellMinerCDB tool allows selection of multiple criteria such as cancer cell line database, drug (y-axis), and gene expression level (x-axis) to quickly produce a visual of a drug's anti-cancer activity, as well as its relationship to molecular variability within those same cell lines. With CellMinerCDB, named entities are transparently matched across sources, allowing cell line molecular features and drug response patterns to be readily compared using bivariate scatter plots and correlation analyses. Multivariate models of drug response or any other cell line attribute can be developed, assessed, and refined. Analyses can be restricted to tissues of origin, with cell lines across all sources mapped to a uniform tissue type hierarchy. Gene pathway annotations allow rapid assessment and filtering of analysis results.

This disclosure presents data integrated within CellMinerCDB and summarizes key features of molecular and drug data reproducibility and complementarity across sources, establishing the data for use in pharmacogenomic analysis. The disclosure also provides examples illustrating the exploration of cancer biology and drug response determinants.

This disclosure provides expanded data available for understanding variability in drug activity profiling by testing 19 compounds from a range of mechanistic classes in the large GDSC cell line panel. Readily accessible scatterplots of matched cell line activity data can either highlight problem areas with particular results, or verify their reproducibility. The cross-database comparison features of CellMinerCDB allow researchers to explore these issues and thus better direct experimental studies. This disclosure also provides the identification of non-cancer drugs oxyphenisatin, oxyphenisatin acetate, and bisacodyl, previously known for their laxative properties as being substantially more active in triple-negative breast cancer lines relative to cancer drugs tested either on the NCI-60 or GDSC panels.

Drug response assays used across the major pharmacogenomic data sources measure different biochemical features over different time scales. However, there is still significant concordance between activity data generated at the NCI and the Sanger Institute. Moreover, for several widely used anticancer drugs, such topotecan and dabrafenib, CellMinerCDB shows there is activity data reproducibility across all major sources.

With both drug activity reproducibility and broader associations between molecular features, such as CDKN2A expression and gene copy/methylation, the inventors found that the NCI-60 database could effectively capture relationships evident in larger cell line sets. The latter better reflect tissue type diversity and associated context-specific molecular features. Still, for dominant associations, such as SLFN11 expression and DNA-targeted drug responses, representative cell line sets such as the NCI-60 are often sufficient. The NCI-60 are also a tractable starting point for molecular data expansion with leading-edge technologies. RNA-Seq data with isoform-specific transcript expression, and SWATH mass spectrometry-based protein expression data have been generated for the NCI-60, and will be made available within both CellMiner and CellMinerCDB.

CellMiner CDB provides data consistent with prior comparative studies demonstrating the efficacy of gene expression data in drug sensitivity prediction. In view of the noted challenges with mutation profiling, gene expression may well provide a sound basis for modeling drug response, particularly when coupled with experimental knowledge of response-related processes.

EXAMPLES

Example 1. Data Source Comparisons

CellMinerCDB currently integrates four cancer cell line data sources (CellMiner NCI-60, Sanger/Massachusetts General Hospital GDSC, the Broad/Novartis CCLE, and the Broad CTRP) and one tissue-specific source focused on 66 small cell lung cancer lines (NCI SCLC). Collectively, these sources provide drug activity and molecular profiling data for approximately 1,400 distinct cancer cell lines (FIG. 2*a*). Each source has particular strengths. The NCI-60 is unmatched with respect to breadth of molecular profiling data, as well as the number of tested drugs. The NCI-60 data also include replicate data readily accessible via the established CellMiner data portal. The GDSC, CCLE, and CTRP sources feature much larger numbers of cell lines, spanning tissues of origin not included in the NCI-60. The range of tested compounds in these expanded cell line panels is narrow relative to the NCI-60, though the GDSC and CTRP include activity data for a wide range of clinically relevant anticancer drugs. The CTRP, in particular, is focused on drug activity profiling, and provides data for 170 FDA-approved or investigational anticancer drugs and 196 other compounds with mechanism of action information. The CTRP molecular data in CellMinerCDB are from the CCLE, which includes the CTRP cell line set.

In spite of ongoing data acquisition and processing efforts, gaps exist with respect to genomic profiling data in sources beyond the CellMiner NCI-60. With the GDSC gene mutation and methylation data, processing pipelines developed for the NCI-60 were used to compute gene-level summary data from publicly available raw data. Remaining source-specific molecular profiling data gaps can be filled within CellMinerCDB by effectively extending data provided by one source to another. This is possible because of substantial overlaps between tested cell lines and drugs (FIG. 2B, C). For example, methylation data are not publicly available for the CCLE, but GDSC methylation data can be utilized for the over 600 CCLE cell lines included in the GDSC (FIG. 2B). Conversely, gene copy number data that are not publicly available from the GDSC can be derived for the cell lines shared with the CCLE (FIG. 2B and see below).

Example 2. Molecular Data Reproducibility

Figure 3:
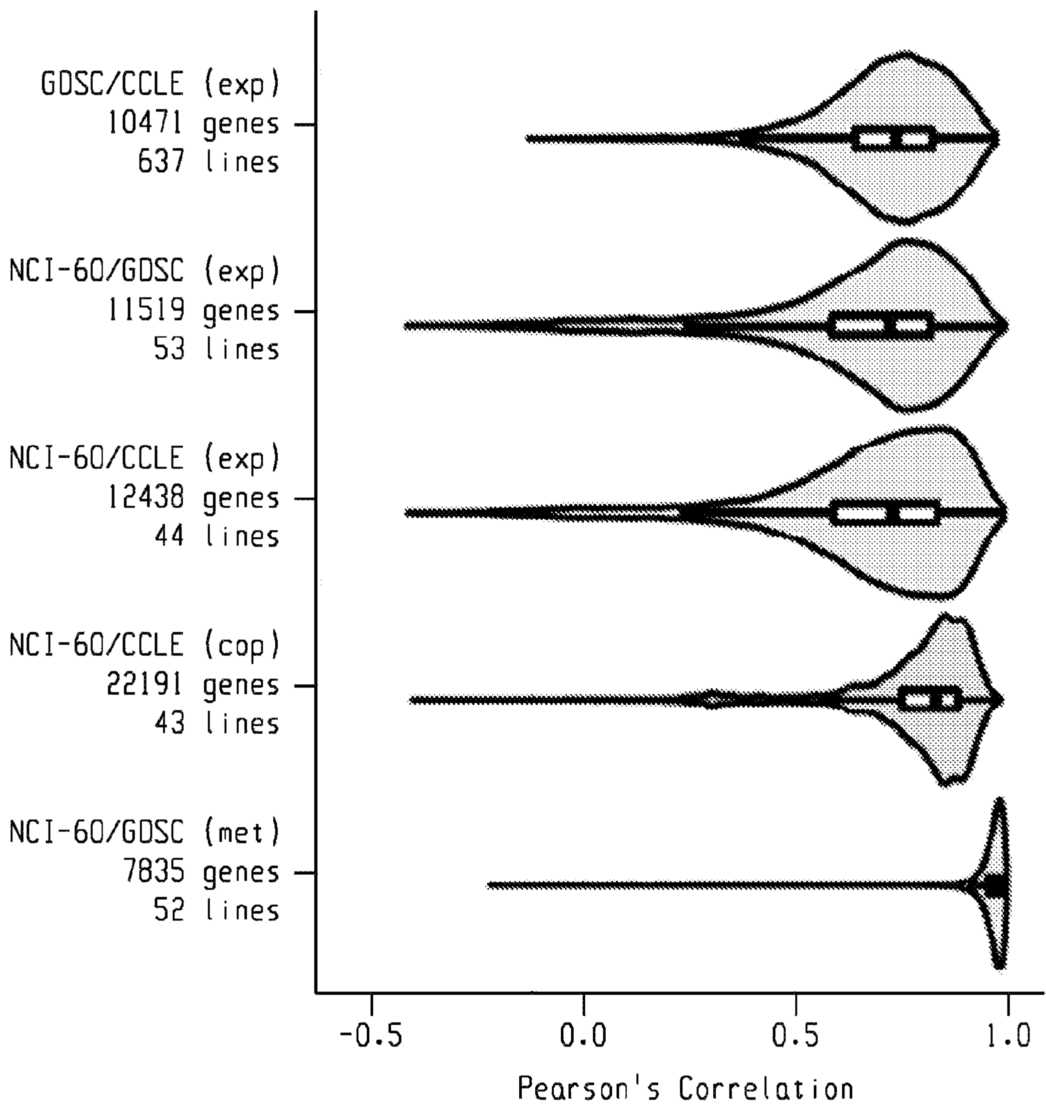
FIG. 3. Molecular data reproducibility. Distributions of gene-level molecular profile similarity measures over cell lines shared between the indicated data sources. Bar plots indicate the median and inter-quartile range. Pearson's correlation distributions for comparable expression (exp), DNA copy number (cop), and DNA methylation (met) data.

Integrative analyses presuppose data concordance across sources. For molecular data, data concordance was systematically assessed by computing the Pearson's correlations between gene-specific molecular profiles over matched cell lines for all pairs of sources and comparable data types. The distributions of expression, copy number, and methylation data correlations indicate substantial concordance across sources (FIG. 3). For these analyses, gene-level patterns with uniformly low values across cell lines were excluded. Gene-level mutation data in CellMinerCDB indicate the probability of a homozygous, function impacting mutation, however, technical, quality control, and reproducibility issues remain currently.

Example 3. Exploring Gene Interactions

Figures 4A, 4B, 4C:
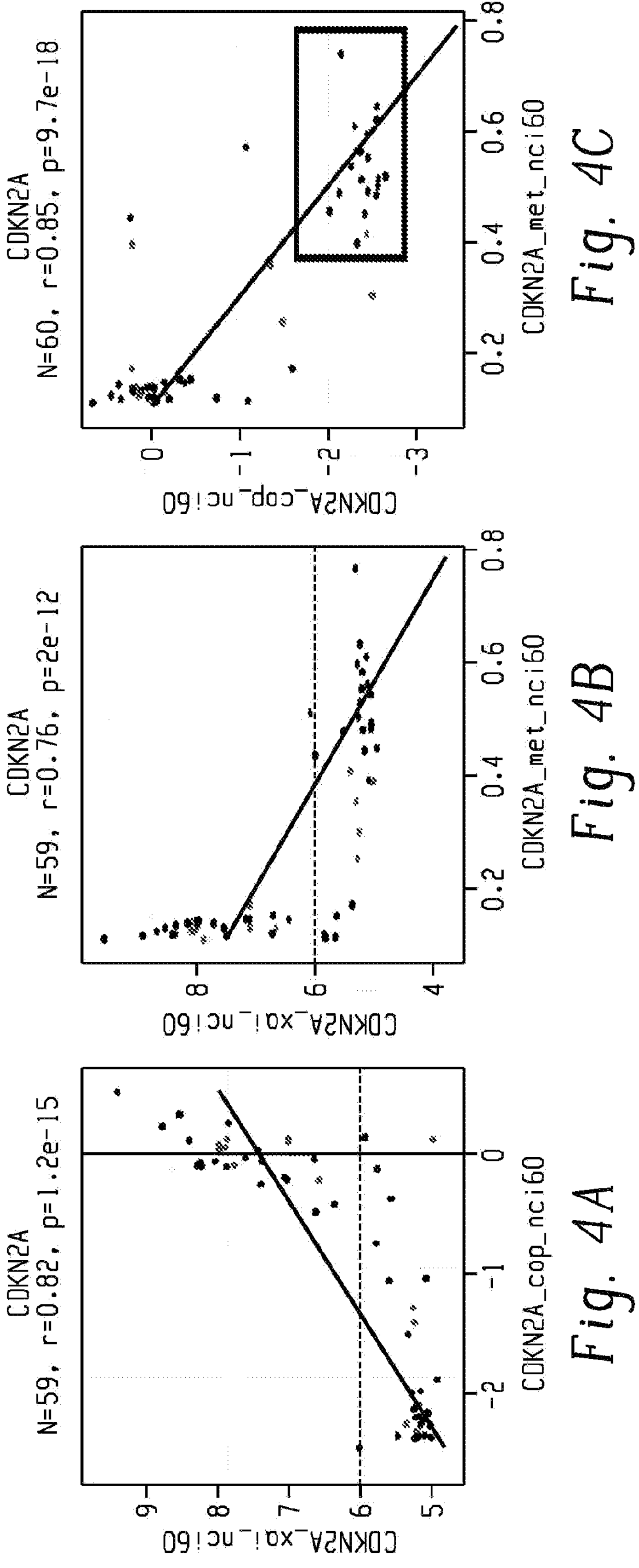
FIG. 4. Exploring gene expression determinants. A. Reduced mRNA expression of the cell cycle inhibitor and tumor suppressor CDKN2A (p16) is associated with DNA copy loss and B. promoter methylation in the NCI-60 cell lines. C. In a subset of NCI-60 lines, enclosed in, these events co-occur. DNA copy number and promoter methylation data from the CCLE and GDSC, respectively, can be integrated over matched cell lines to verify a similar pattern in larger cell line collections (D, E, F). G. DNA copy number gain is associated with increased expression of the oncogenes MYC and H. KRAS in selected CCLE cell lines. In G, small cell lung cancer lines are indicated in light gray to highlight a subset potentially derived from MYC-driven tumors (within dashed box).
Figures 4D, 4E, 4F:
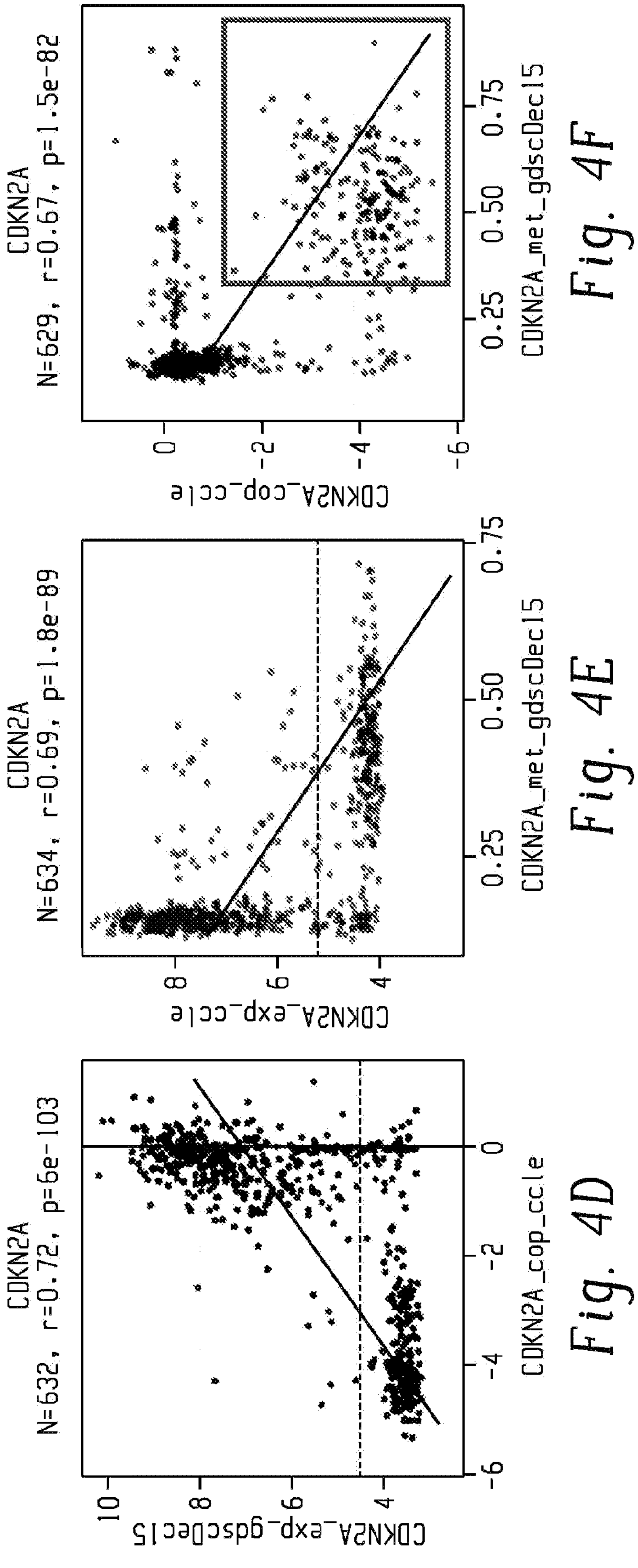
Figure 4H:
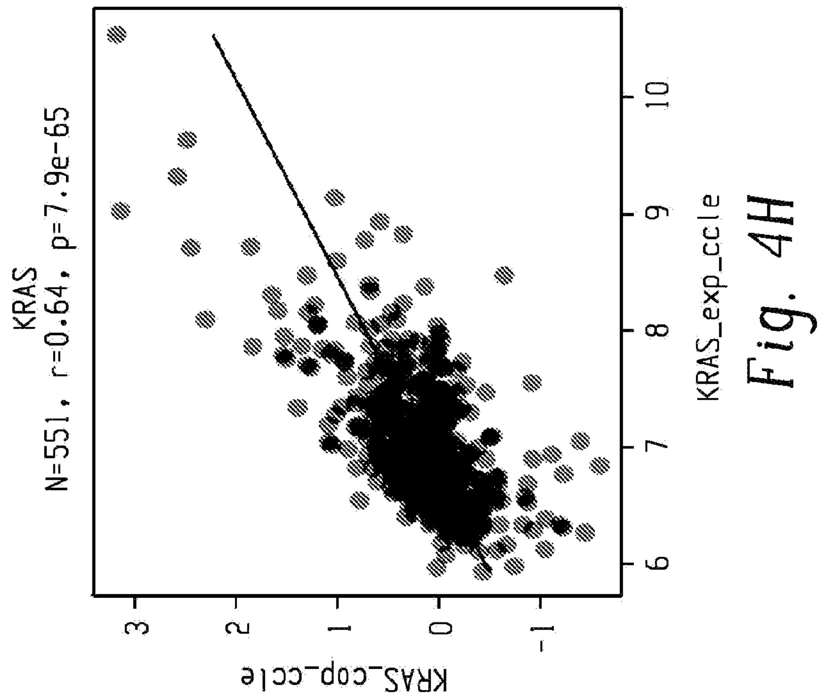
Figure 4G:
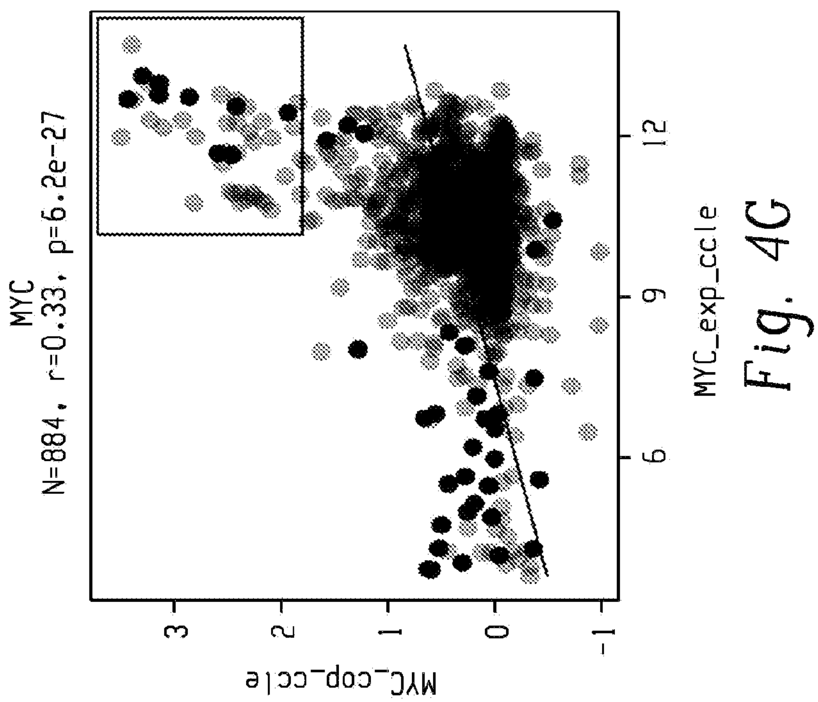

The ability to identify and quantitate interactions among genes allows one to assess putative influences within cells. In cancer, specific gene expression is often altered by promoter methylation or DNA copy number changes. CellMinerCDB provides a way to identify these and other gene interactions. In the NCI-60, reduced expression of the tumor suppressor gene CDKN2A (p16) (y-axis) is associated with both DNA copy loss (x axis) (FIG. 4*a*) and promoter methylation (FIG. 4*b*). Moreover, FIG. 4*c* shows that approximately 25% of cell lines show both of these alterations, consistent with bi-allelic, 'two-hit' suppression of CDKN2A expression. Validation of this result is provided by the integration of GDSC methylation data and CCLE DNA copy number data (FIG. 4*d-f*). The impact of copy gain on increased oncogene expression can be similarly assessed. For example, a subset of potentially MYC-driven CCLE small cell lung cancer lines show both MYC copy gain and increased MYC gene expression (FIG. 4*g*). KRAS activation, typically regarded as mutation-driven, may also occur by copy gain, as evident in a subset of CCLE lines (FIG. 4*h*), as well as in clinical studies.

Example 4. Drug Activity Data Reproducibility and Enrichment

Figure 5B:
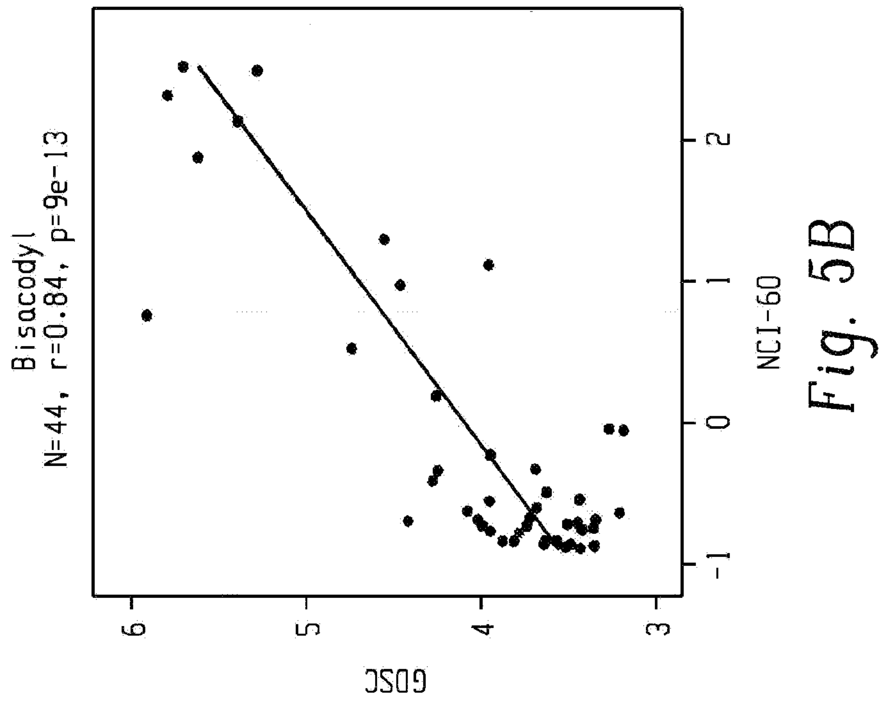
FIG. 5. Drug activity data reproducibility. A. NCI-60 (x-axis) versus GDSC (y-axis) drug activity data in matched cell lines for Acetalax. B. NCI-60 (x-axis) versus GDSC (y-axis) drug activity data in matched cell lines for Bisacodyl.
Figure 5A:
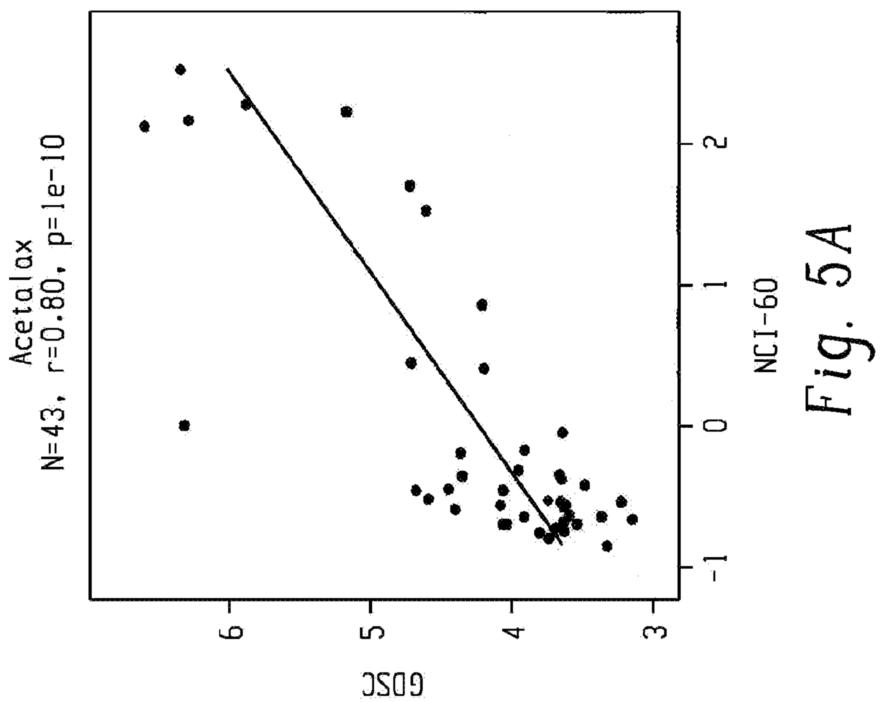

To determine reproducibility across institutes and assay types, we tested a selected set of NCI-60-screened compounds for activity in the GDSC cell line panel (Table 1). Drug data reproducibility may be affected by potential sources of data divergence such as assay type and duration for drug treatment. Noting that the GDSC and the NCI/DTP used different assays to determine their IC50 values (Cell Titer Glo measurements of ATP at 72 hours post-treatment versus sulforhodamine B measurement of total protein at 48 hours post-treatment), we compared 19 drugs referenced by their NSCs (National Service Center identifiers) and associated with a range of mechanisms of action types. The drugs with the strongest correlations were oxyphenisatin acetate (Acetalax) (FIG. 5*a*, $R=0.80$, $p=1.1\times10^{-10}$, $N=43$) and bisacodyl (FIG. 5*b*, $R=0.84$, $p=9.0\times10^{-13}$, $N=44$). These FDA-approved laxatives lacked pre-existing data in the CTRP, CCLE and GDSC.

TABLE 1

Comparison of drug activities as measured by GDSC and DTP

| Drug name | Mechanism of action | Correlations[b] | p-value |
|---|---|---|---|
| Oxaliplatin | Alkylating agent | 0.529 | 4.46E−04 |
| Carmustine | Alkylating agent | 0.471 | 1.25E−03 |
| BEN | Alkylating agent | 0.453 | 4.90E−03 |
| Actinomycin D | DNA binder | 0.417 | 4.85E−03 |
| Bleomycin sulfate | DNA binder | 0.503 | 5.05E−04 |
| Fludarabine phosphate | DNA synthesis inhibitor | 0.379 | 1.12E−02 |
| Nelarabine | DNA synthesis inhibitor | 0.769 | 4.38E−09 |
| Romidepsin | Histone deacetylase | 0.407 | 7.50E−03 |
| Dacarbazine | A7\|Ho\|AlkAglanti-Ho | −0.013 | 9.41E−01 |
| Fulvestrant | Hormone | 0.255 | 9.82E−02 |
| Topotecan hydrochloride | Topoisomerase 1 inhibitor | 0.625 | 5.84E−06 |

TABLE 1-continued

Comparison of drug activities as measured by GDSC and DTP

| Drug name | Mechanism of action | Correlations[b] | p-value |
|---|---|---|---|
| MJ-III-65 | Topoisomerase 1 inhibitor | 0.662 | 9.84E−07 |
| Teniposide | Topoisomerase 2 inhibitor | 0.648 | 1.98E−06 |
| Mitoxantrone | Topoisomerase 2 inhibitor | 0.603 | 1.48E−05 |
| Vincristine sulfate | Tubulin affecting | 0.208 | 1.80E−01 |
| Docetaxel | Tubulin affecting | 0.494 | 2.18E−03 |
| Zoledronic acid (Zometa) | Antimetabolite | 0.339 | 2.61E−02 |
| Bisacodyl | Laxative | 0.841 | 9.00E−13 |
| Oxyphenisatin acetate (Acetalax) | Laxative | 0.801 | 1.10E−10 |

[a]Food and Drug Administration approved drugs GI50 activities as measured by the Developmental Therapeutics Program (DTP, http://dtp.nci.nih.gov/) using the sulforhodamine B assay of total protein
[b]Pearsons correlations between the GDSC −log10 activity data, and CellMiner drug activity z scores.

Figure 6A:
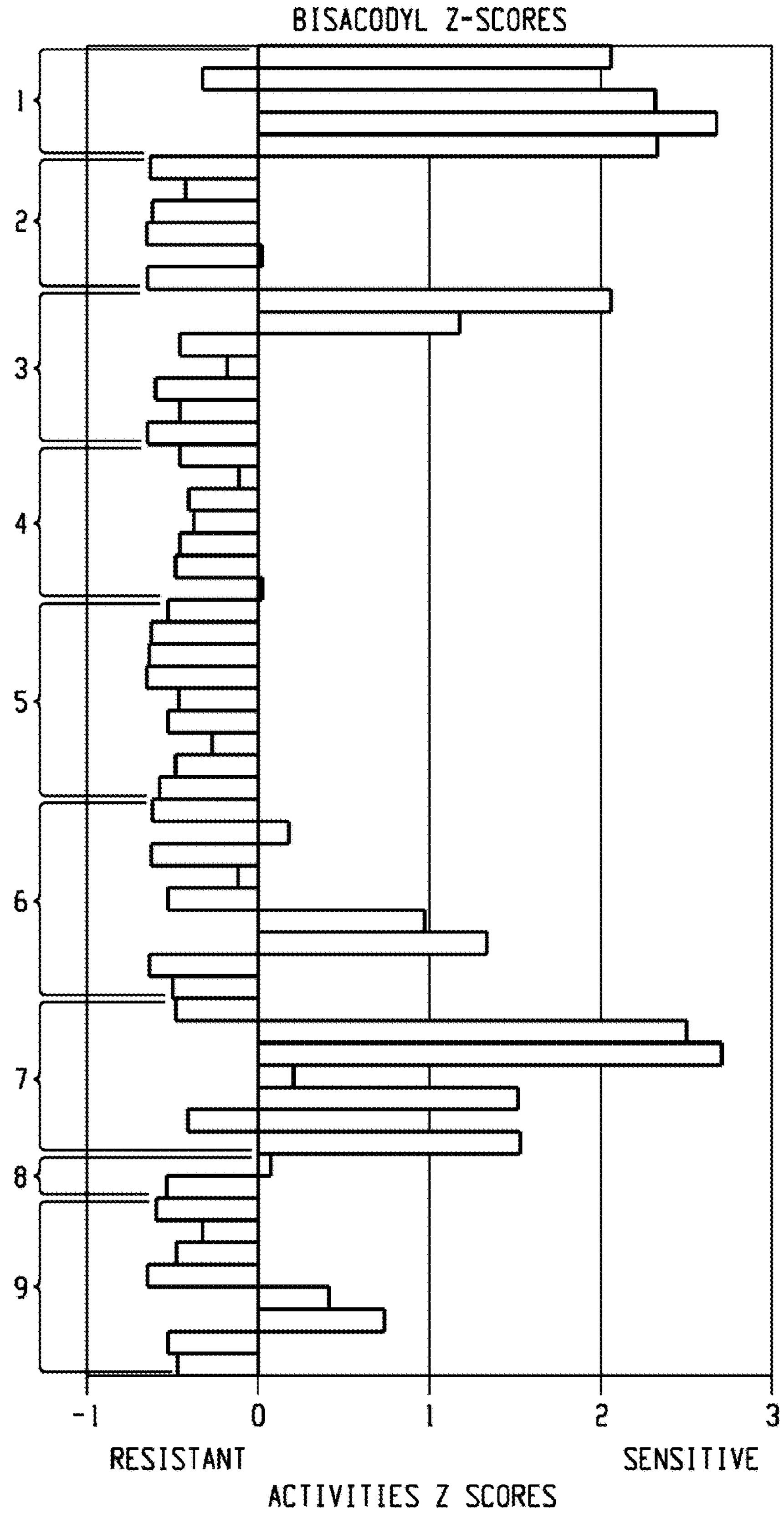
FIG. 6A, bisacodyl activity and FIG. 6B, Acetalax activity against NCI-60 cell lines. Activity is represented by Z score. Bisacodyl and Acetalax showed very similar activity patterns with strong efficacy against certain breast cancer, colorectal cancer, and ovarian cancer cell lines.
Figure 6B:
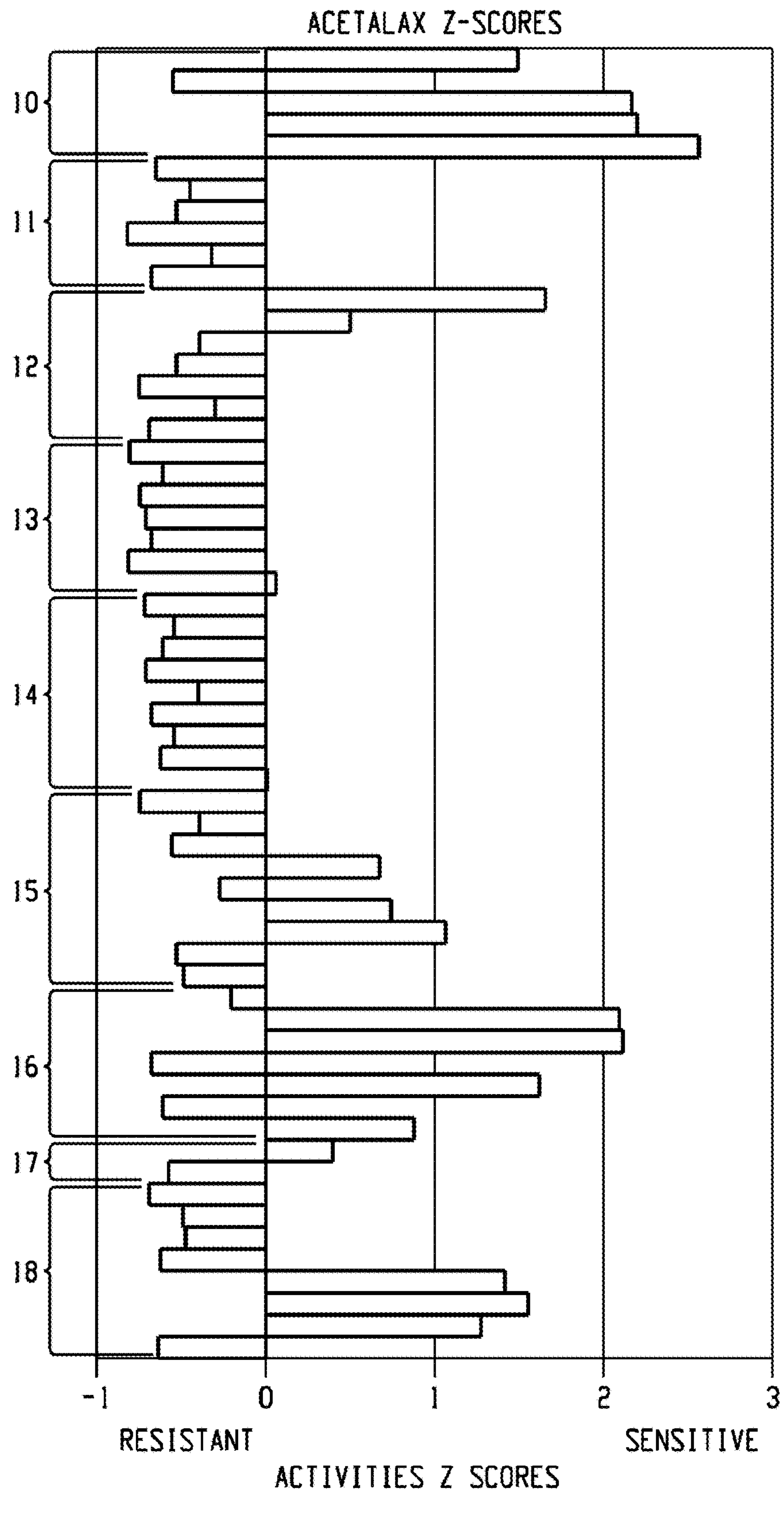
In FIG. 6B group 10 cell lines are breast cancer cell lines, group 12 are colon cancer cell lines, and group 16, are ovarian cancer cell lines.

Example 5. Additional Characterization of Bisacodyl and Acetalax as Anti-Cancer Agents Acetalax and bisacodyl activities against a number of NCI-60 cell lines were obtained. Z scores for bisacodyl are shown in FIG. 6A and for Acetalax are shown in FIG. 6B. Both compounds showed similar activity patterns with robust activity against 4 of 5 tested breast cancer cell lines (MCF7, HS578T, BT549, and T47D), two of seven colorectal cell lines (COLO205 and HCC2998), and four of seven ovarian cancer cell lines (OVCAR-3, OVCAR-4, OVCAR-8) and NCI-ADR-RES). The activities of Acetalax versus bisacodyl in NCI-60 cell lines were plotted (data not shown) and found to exhibit a strong correlation; Pearson correlation (r)=0.92, p-value=1.3-24. The NCI-60 cell lines evaluated in FIGS. 6A and B are listed in Table 2.

TABLE 2

| FIG. 6A Group (bisacodyl) | FIG. 6B Group (Acetalax) | Cell Lines (from top to bottom of figure) | Tissue Type |
|---|---|---|---|
| 1 | 10 | MCF7 | Breast |
| | | MDA MB 231 | |
| | | HS578T | |
| | | BT 549 | |
| | | T47D | |
| 2 | 11 | SF 268 | CNS |
| | | SF 295 | |
| | | SF 539 | |
| | | SNB 19 | |
| | | SNB 75 | |
| | | U251 | |
| 3 | 12 | COLO205 | Colon |
| | | HCC 2998 | |
| | | HCT 116 | |
| | | HCT 15 | |
| | | HT29 | |
| | | KM12 | |
| | | SW 620 | |
| 4 | 13 | CCRF CEM | Blood (leukemia) |
| | | HL 60 | |
| | | K 562 | |
| | | MOLT 4 | |
| | | RPMI 8226 | |
| | | SR | |
| 5 | 14 | LOX IMVI | Skin (melanoma) |
| | | MALME 3M | |
| | | M14 | |
| | | SK MEL 2 | |
| | | SK MEL 28 | |
| | | SK MEL 5 | |
| | | UACC 257 | |
| | | UACC 62 | |
| | | MDA MB 435 | |
| | | MDA N | |
| 6 | 15 | A549 | Lung |
| | | EKVX | |
| | | HOP 62 | |
| | | HOP 92 | |
| | | NCI H226 | |
| | | NCI H23 | |
| | | NCI H322M | |
| | | NCI H460 | |
| | | NCI H522 | |
| 7 | 16 | IGROV1 | Ovarian |
| | | OVCAR 3 | |
| | | OVCAR 4 | |
| | | OVCAR 5 | |
| | | OVCAR 8 | |
| | | OV 3 | |
| | | NCI ADR RES | |
| 8 | 17 | PC 3 | Prostate |
| | | DU 145 | |
| 9 | 18 | 786 0 | |
| | | A498 | |
| | | ACHN | |
| | | CAKI 1 | |
| | | RXF 393 | |
| | | SN12C | |
| | | TK 10 | |
| | | UO 31 | |

Figures 7A, 7B:
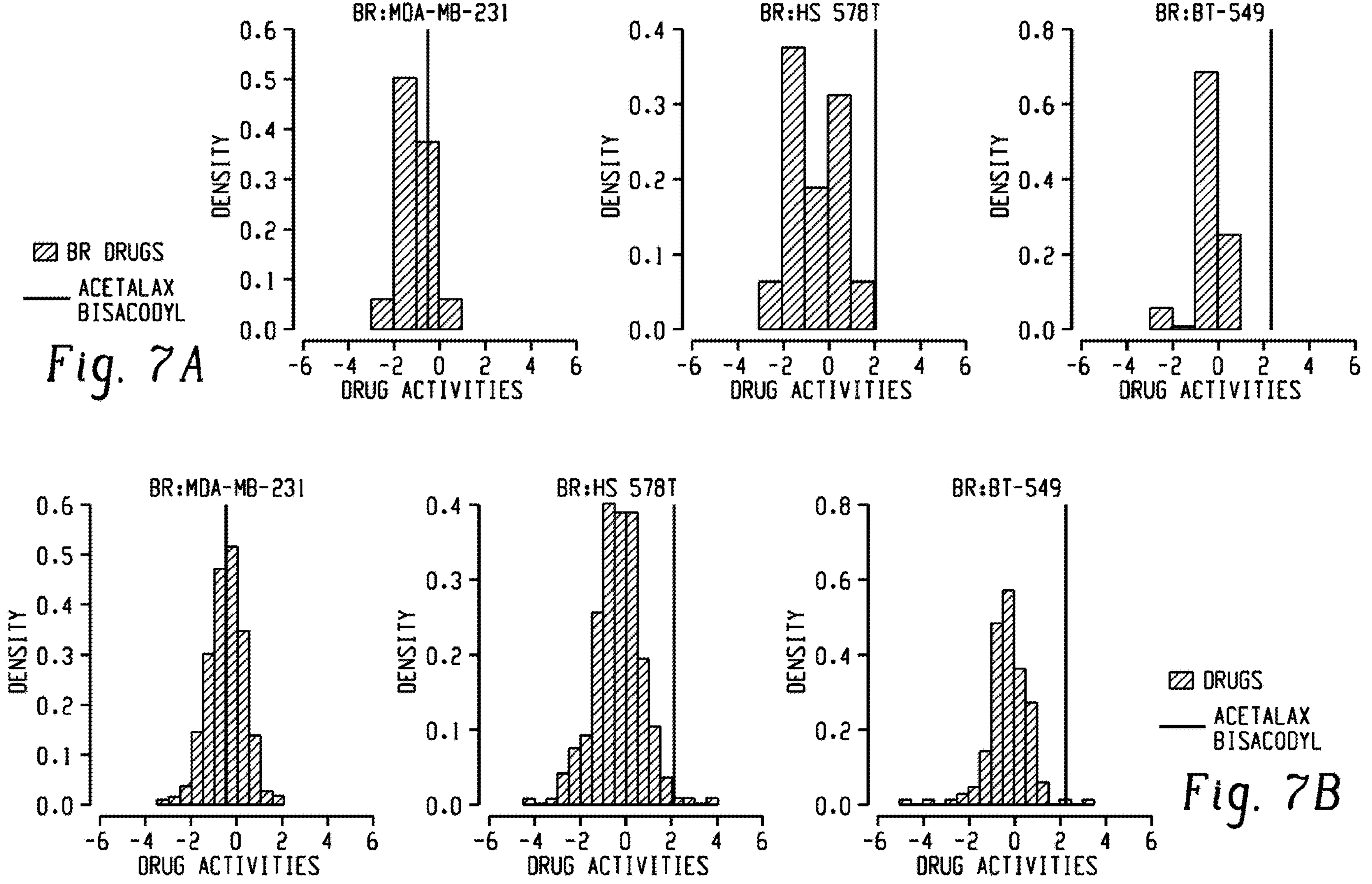
FIG. 7. Comparison of Acetalax and bisacodyl (which are represented together by the dark line) activity to that of known anticancer drugs in triple negative cancer cell lines. A. The comparison of Acetalax and bisacodyl activity against the MDA-MB-231, HS 578T, and BT-549 triple negative breast cancer cell lines to that of 13 anti-breast cancer drugs. B. The comparison of Acetalax and bisacodyl activity to that of 201 FDA approved or clinical trial drugs.

These test in the NCI-60 showed that in two of the three NCI-60 triple negative breast cancer cell lines (HS 578T and BT-549), the non-cancer drugs Acetalax and bisacodyl, were more effective than 13 approved breast cancer drugs (FIG. 7A). The breast cancer drugs tested were capecitabine, carboplatin, cyclophosphamide, docetaxel, doxorubicin, epirubicin, fluorouracil (5FU), gemcitibine, methotrexate, mitomycin, mitoxantrone, paclitaxel, and vincristine. Expanding the analysis to all available (~178) FDA-approved breast cancer drugs, Acetalax and bisacodyl were again found to have superior anticancer activity against the same two NCI-60 cell lines (FIG. 7B). This suggested that some significant subset of triple negative breast cancers were preferentially sensitive to these drugs.

Figures 8A, 8B:
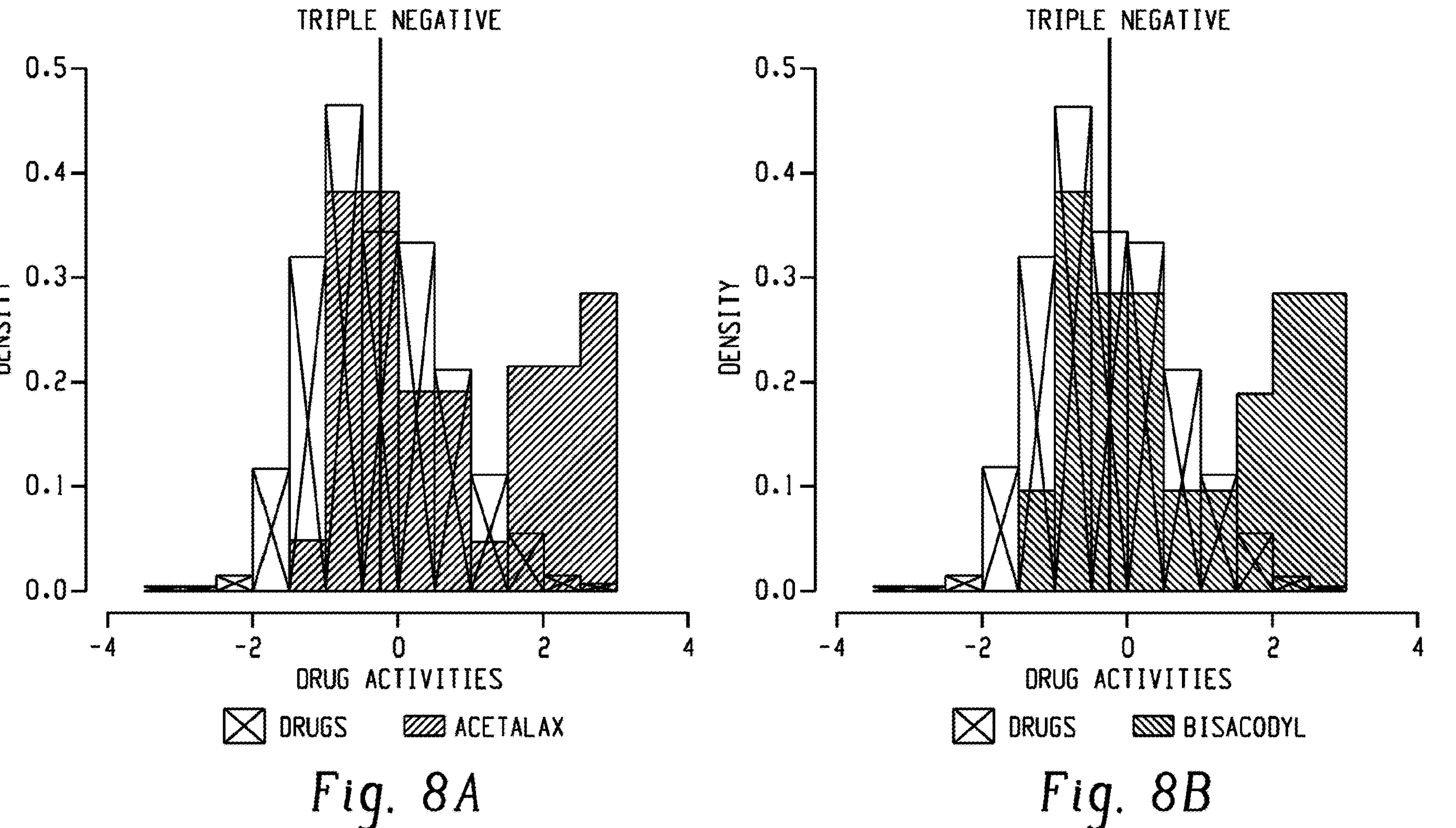
FIG. 8. Density plot of Acetalax or bisacodyl activity against a panel of 21 triple negative breast cancer cell lines, Nineteen unrelated anti-cancer drugs were used as controls. A. The comparison of Acetalax activity (diagonally lined rectangles) to the activity of 19 anti-cancer drugs against triple negative breast cancer cell lines. B. The comparison of bisacodyl activity (cross hatched rectangles) to the activity of 19 anti-cancer drugs against triple negative breast cancer cell lines.

We validated and expanded this result using the Acetalax and bisacodyl tested in the GDSC cell line panel (Table 1). In this work, the drugs were assessed in a different institution using a different assay using 1,080 cell lines, including 21 triple negative breast cancers (FIG. 8A, B). At the technical level, the results were very consistent. Similar results were obtained within the GDSC database for the Acetalax and bisacodyl activities, with robust correlation (Pearson's) of (r)=0.92, p-value $1.1^{-297}$. The activity of Acetalax in GDSC vs the NCI-60 has a Pearson correlation of (r)=0.8, p-value $1.1^{-10}$. The activity of bisacodyl in the GDSC database cell lines vs NCI-60 cell lines has a Pearson correlation of (r)=0.82, p-value $8.3^{-12}$. The data from the 19 cancer drugs (shown as clear rectangle) as compared to Acetalax and bisacodyl (shown as diagonally lined rectangles) indicates their relative activities. For the Acetalax and bisacodyl there is a clear bimodal split of the triple negative cancers, indicating comparable activities to the cancer drugs for a some of the triple negatives (the left peak), and clearly superior activity for the others (the right peak).

The GDSC results confirmed and extended our NCI-60 observations, showing that both Acetalax and bisacodyl elicited a broad range of cytotoxic responses in the expanded GDSC cell line collection, in addition to being more active than any of the oncology drugs by a significant margin ($p<7E-10$) in the triple negative breast cancer lines.

Figure 9A:
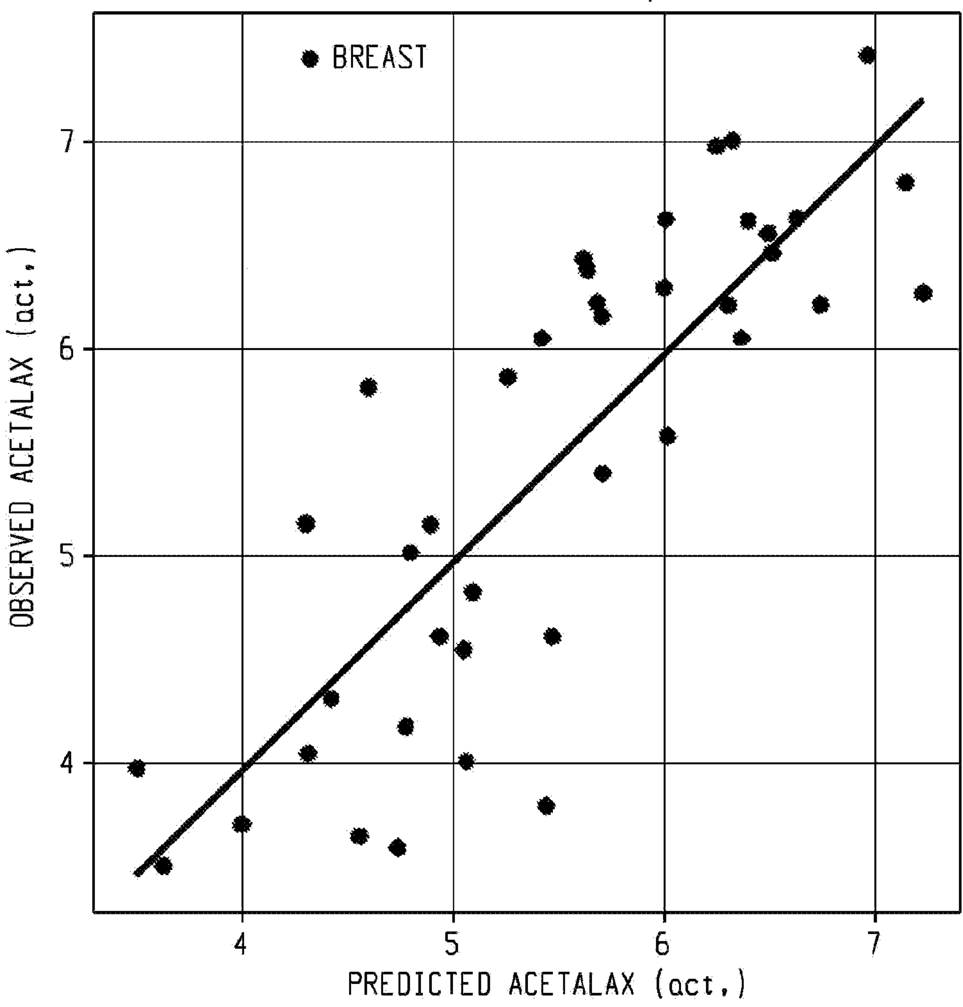
In FIG. 9A predictions were based on the transcript expression levels of IGF1 (an apoptosis factor), SCL31A1 (a solute carrier), and ABCA12 (an ABC transporter).
Figure 9B:
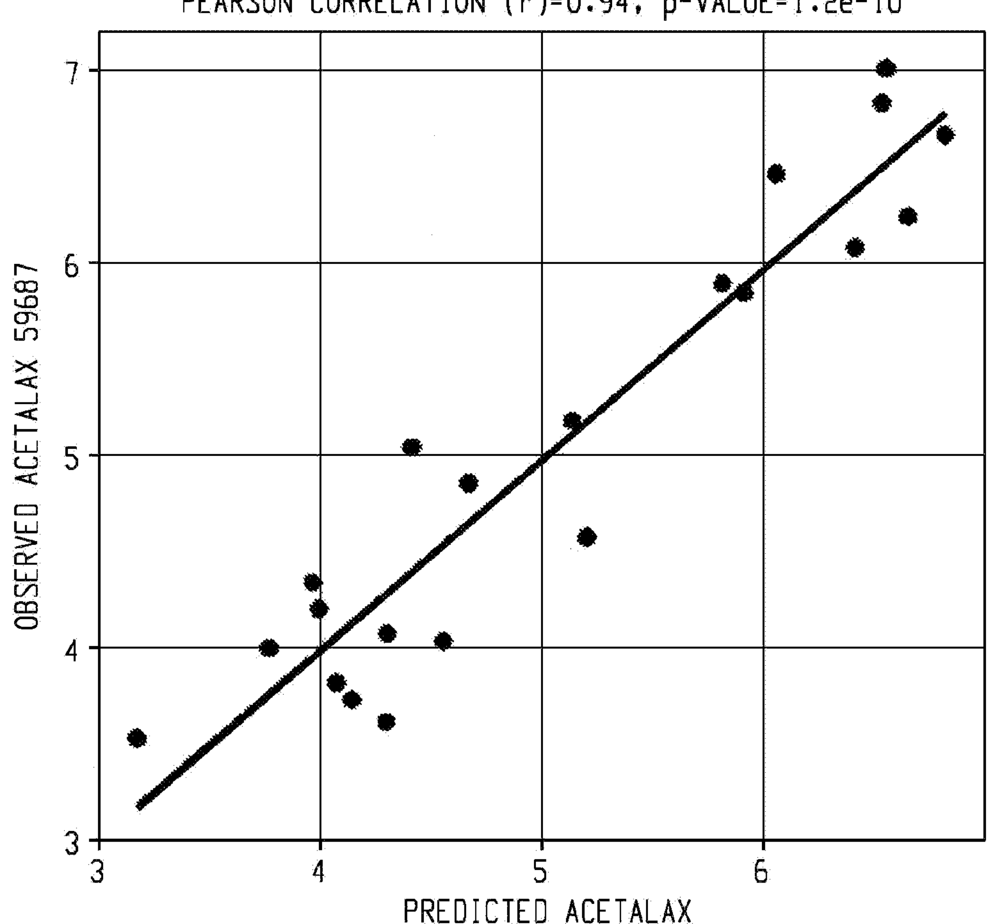
In FIG. 9B the cell lines were restricted to the triple negative breast cancer cell lines, and predictions were based on the transcript expression levels of IGF1, SPIB (a transcription factor), SCL31A1, and ABCA12, and PIK3R1 (a survival gene from the EGFR/ERBB2 pathway).

Example 6. Construction of Model for Biomarker Prediction for Bisacodyl and Acetalax in Triple Negative Breast Cancers Acetalax activity in GDSC breast cancer cell lines was predicted based on the activity of this compound against IGF1 (an apoptosis factor), SCL31A1 (a solute carrier), and ABCA12 (an ABC transporter). Predicted activity was strongly correlated with observed Acetalax activity, Pearson correlation (r)=0.82, p-value $3.5^{-11}$ (FIG. 9A). Predicted and observed activity was even more strongly correlated in GDSC triple negative breast cancer cell lines, with the addition of SPIB (a transcription factor) and PIK3R1 (a survival gene in the EGFR ERBB2 pathway) (FIG. 9B), Pearson correlation (r)=0.94, p-value=1.2-10.

General Methods

NCI-60 Data

NCI-60 drug activity, molecular profiling, and annotation data was obtained from CellMiner (Database Version 2.1). The latest versions of these data can also be downloaded from the CellMiner site (discover.rtci.nih.gov). Detailed information about CellMiner data preparation is publically available for example, in Reinhold, W. C. et al., *Cancer Res.* 72:3499-3511 (2012), Reinhold, W. C. et al., *Cancer Res.* 77:601-612 (2017), Abaan, O. D. et al., *Cancer Res.* 73:4372-4382 (2013), and Varma, S. et al., *PloS One* 9: e92047 (2014), as well as being documented within CellMiner. Essential attributes of the NCI-60 data made available within CellMinerCDB are summarized below.

COMPOUND ACTIVITY. Compound activity is indicated as a standardized, 'z-score' value derived from measurement of the cell line-specific 50% growth-inhibitory (GIS0) concentration using the sulforhodamine B total protein cytotoxicity assay generated by the Developmental Therapeutics Program (dtp.cancer.gov). In particular, for each compound, the mean and standard deviation of −log 10 [molar GI50] values over the NCI-60 lines are used to center and scale the data.

TRANSCRIPT EXPRESSION. Transcript expression for each gene was determined through integration of relevant probe-level data from 5 microarray platforms, as described in Reinhold, W. C. et al., *Cancer Res.* 72:3499-3511 (2012). Data are provided in both standardized 'z-score' form, derived as described above for the drug activity data, and as average log 2 intensities.

DNA COPY NUMBER. DNA copy data were integrated from four array-CGH platforms. Numerical values indicate the average log 2 probe intensity ratio for the cell line (gene-specific chromosomal segment) DNA relative to normal DNA.

DNA METHYLATION. DNA methylation data were obtained using the Illumina Infinium Human Methylation 450 platform. Numerical values indicate the average of the beta values for a gene-associated probes. Beta values lie between 0 (lack of methylation) and 1 (complete methylation).

MICRORNA EXPRESSION. MicroRNA expression data were obtained using the Agilent Technologies Human miRNA Microarray V2. Numerical values indicate the average log 2 probe intensity.

COMPOUND ACTIVITY. Preprocessed activity data for 256 compounds were downloaded from the GDSC site (http://www.cancerrxgene.org/downloads). An additional 41 compounds were selected for testing on the GDSC cell lines based on current therapeutic use, potential for repurposing, or as novel candidates for further mechanistic investigation. The latter compounds were selected based on their unique activity patterns in the NCI-60. GDSC-provided activity values were converted to indicate the −log 10 [molar IC50].

TRANSCRIPT EXPRESSION. Raw Affymetrix Human Genome U219 microarray data deposited in ArrayExpress (E-MTAB-3610) was processed using RMA normalization. Probe-to-gene mapping was performed using the BrainArray CDF file for the Affymetrix HG-U219 platform, available at brainarray.mbni.med.umich.edu. Numerical values summari e gene-specific log 2 probe intensities. Additional platform and processing details are provided in Iorio, F. et al., *Cell* 166: 740-754 (2016).

DNA METHYLATION. The table of pre-processed beta values for all CpG islands across the GDSC cell lines was downloaded from the supplementary resources site associated with (www.cancerrxgene.org). As with the NCI-60 data, GDSC DNA methylation data were obtained using the Illumina Infinium Human Methylation 450 platform, and gene-level methylation values were computed using the approach utilized with the NCI-60 data (indicated above).

DETERMINATION OF PROSPECTIVE TRIPLE NEGATIVE BREAST CANCERS. Transcript expression levels of ERBB2, ESR1, ESR2 and PGR (HER2, estrogen receptor and progesterone receptor) were assessed by GDSC using the Affymetrix Human Genome U219 Array and accessed in CellMinerCDB. Cell lines with a low value for all three genes were classified as triple negative. The log 2 intensity thresholds used were ERBB2<5, ESR1<3.5, and PGR<3. ESR2 had low expression in all breast cell lines.

CCLE Data

CCEE data were downloaded from portals.broadinstitute.org, and are further described in J. Barretina et al., *Nature* 483:603-607 (2012).

COMPOUND ACTIVITY. Drug activity profiles are available for 24 compounds. CCLE-provided activity values were converted to indicate the −log 10 [molar IC50].

TRANSCRIPT EXPRESSION. Raw CEL file data derived from the Affymetrix U133+2 platform were downloaded from the CCLE portal. Normalization was performed using the frma method, implemented by the corresponding Bioconductor package, McCall, M. N. et al., *Biostatistics* 11, 242-253 (2010). Numerical values are the average of gene-specific log 2 probe intensities, with the gene-to-probe-set mapping obtained from the hgu133plus2.db Bioconductor package.

DNA COPY NUMBER. Gene-level copy number data derived from the Affymetrix SNP 6.0 array were downloaded from the CCLE portal. Numerical values are normalized log 2 ratios, i.e., log 2 (CN/2), where CN is the estimated copy number.

CTRP Data

CTRP compound activity data for 481 compounds across 823 cell lines were obtained from Supplementary Tables S2, S3, and S4 of Rees, M. G. et al., *Nat. Chem. Biol.* 12:109-116 (2016). Cell line activity data originally indicated the area under a 16-point dose response curve (AUC). These values were subtracted from the maximum observed AUC value (over all cell lines and drugs) to represent CTRP activity in CellMinerCDB by the estimated area above the dose-response curve. This transformation allows increased drug sensitivity to be associated with larger values of the activity measure, consistent with other source activity data integrated within CellMinerCDB. The above CTRP cell line set is included in the CCLE, and CCLE molecular data are thus used for CTRP analyses in CellMinerCDB.

NCI-SCLC Data

Compound activity and transcript expression data for the NCI-SCLC data set were downloaded from sclccelllines-dev.cancer.gov. Provided activity values were converted to indicate the −log 10 [molar IC50]. Transcript expression values are derived from log 2 microarray probe intensities.

CellMinerCDB Analyses

Molecular or drug response patterns across sets of cell lines can be plotted with respect to one another within the 'Univariate Analyses-Plot Data' tab. From the 'Univariate Analyses-Compare Patterns' tab, additional molecular and drug response correlates can be tabulated, with respect to either the plotted x-axis or y-axis variable. Pearson's correlations are provided, with reported p-values not adjusted for multiple comparisons. The 'Regression Models' tab set allows construction and assessment of multivariate linear models. The response variable can be set to any data source-provided feature (e.g., a specific cell line drug response or gene expression profile). Basic linear regression models are implemented using the R stats package Im( ) function, while lasso (penalized linear regression models) are implemented using the glmnet R package. The lasso performs both variable selection and linear model coefficient fitting. The lasso lambda parameter governs the tradeoff between model fit and variable set size. Lambda is set to the value giving the minimum error with 10-fold cross-validation. For either standard linear regression or LASSO models, 10-fold cross validation is applied to fit model coefficients and predict response, while withholding portions of the data to better estimate robustness. The plot of cross-validation-predicted vs. actual response values can also be viewed within CellMinerCDB, to assess model generalization beyond the training data.

Additional predictive variables for a multivariate linear model can be selected using the results provided within the 'Regression Models-Partial Correlation' tab. Conceptually, the aim is to identify variables that are independently correlated with the response variable, after accounting for the influence of the existing predictor set. Computationally, a linear model is fit, with respect to the existing predictor set, for both the response variable and each candidate predictor variable. The partial correlation is then computed as the Pearson's correlation between the resulting pairs of model residual vectors (which capture the variation not explained by the existing predictor set). The p-values reported for the correlation and linear modeling analyses assume multivariate normal data. The two-variable plot feature of CellMiner-CDB allows informal assessment of this assumption, with clear indication of outlying observations. The reported p-values are less reliable as the data deviate from multivariate normality.

Metadata

Cell lines of particular tissue or tumor types can be highlighted in two-variable plots. In addition, correlation and regression analyses can be restricted to cell line subsets by either inclusion or exclusion of selected tissue or tumor types. To enable this, all cell lines across data sources were mapped to the four-level OncoTree cancer tissue type hierarchy developed at Memorial Sloan-Kettering Cancer Center (www.cbioportal.org). Every cell line has an OncoTree level one specification, such as 'Lung', indicating its tissue of origin. Additional OncoTree levels provide more detailed annotation, distinguishing, for example, small cell lung cancer and various types of non-small cell lung cancer. Within the 'Regression Models' tab set, LASSO and partial correlation analyses can be restricted to gene sets curated by the NCI/DTB Genomics and Bioinformatics Group.

What is claimed is:

1. A method of treating triple negative breast cancer in a patient, comprising administering a therapeutically effective amount of a compound selected from bisacodyl and pharmaceutically acceptable salts and hydrates thereof to the patient.

2. The method of claim 1, wherein the therapeutically effective amount of the compound is an amount sufficient to produce a decrease in the number and/or size of tumors in the patient.

3. The method of claim 1, wherein the therapeutically effect amount of the compound is a total daily dose of 1 mg to 100 mg.

4. The method of claim 3, wherein the daily dose is administered for at least 5 consecutive days.

5. The method of claim 1, wherein the compound is administered subcutaneously or intravenously.

6. The method of claim 1, wherein the compound is a first active compound and is administered in combination with at least one additional active compound.

7. The method of claim 6, wherein the additional active compound is an anthracycline class drug, a taxane class drug, an antimetabolite, an alkylating agent, a platinum agent, or a *vinca* alkaloids.

8. The method of claim 6, wherein the additional active compound is daunorubicin, doxorubicin, epirubicin, idarubicin, valrubicin, docetaxel, paclitaxel, abraxane, taxotere, 5-fluorouracil, 6-mercaptopurine, capecitabine, cytarabine, gemcitabine, mechlorethamine, cyclophosphamide, chlorambucil, melphalan, ifosfamide, cisplatin, carboplatin, oxaliplatin, nedaplatin, vinblastine, vincristine, vindesine, vinorelbine, vincaminol, vineridine, or vinburnine.

9. The method of claim 1, wherein the compound is administered for a period of 1 to 10 weeks and the amount and frequency of dosage is such that concentration of the compound in the patient's plasma is never less than 50% of the patient's plasma Cmax.

10. The method of claim 1, wherein the patient is a candidate for surgery.

11. The method of claim 10, wherein the patient has surgery approximately 1 to 4 months after last treatment with the compound.

12. The method of claim 1, wherein the patient is also treated with radiation therapy.

13. The method of claim 1, wherein the patient has a BRACA1 or BRACA2 mutation.

14. The method according to claim 1, wherein the patient has a tumor that has elevated expression of IGF1, SCL31A1, ABCA12, SPIB, or PIK3R1.

15. The method according to claim 1, wherein the patient has a tumor that has reduced levels of cellular ATP.

16. A method of treating a patient having triple negative breast cancer, the method comprising (a) determining whether the patient has a tumor that has elevated expression of IGF1, SCL31A1, ABCA12, SPIB, or PIK3R1; and (b) if the patient has a tumor that has elevated expression of IGF1, SCL31A1, ABCA12, SPIB, or PIK3R1; and administering a compound selected from oxyphenisatin acetate, oxyphenisatin, bisacodyl, and the pharmaceutically acceptable salts and hydrates of any of the foregoing to the patient.

17. The method of claim 16, wherein the method comprises determining whether the patient has a tumor that has elevated expression of IGF1, SPIB, or PIK3R1; and if the patient has a tumor that has elevated expression of IGF1, SPIB, or PIK3R1; and administering a compound selected from oxyphenisatin acetate, oxyphenisatin, bisacodyl, and the pharmaceutically acceptable salts and hydrates of any of the foregoing to the patient.

18. The method of claim 17, wherein the compound is selected from oxyphenisatin acetate, oxyphenisatin, and the pharmaceutically acceptable salts and hydrates thereof.

19. The method of claim 17, wherein the compound is selected from oxyphenisatin acetate, oxyphenisatin, and the pharmaceutically acceptable salts and hydrates thereof.

20. A method of treating triple negative breast cancer in a patient, comprising administering a therapeutically effective amount of a compound selected from bisacodyl and pharmaceutically acceptable salts and hydrates thereof to the patient, wherein the patient has a tumor that has elevated expression of SCL31A1, ABCA12, SPIB, or PIK3R1.

* * * * *